United States Patent
Osada et al.

(10) Patent No.: US 7,528,169 B2
(45) Date of Patent: May 5, 2009

(54) SUBSTANCE HAVING ANTITUMOR/ANTI-INFLAMMATORY ACTIVITY

(75) Inventors: Hiroyuki Osada, Saitama (JP); Hideaki Kakeya, Saitama (JP); Hiroshi Konno, Akita (JP); Susumu Kanazawa, Kanagawa (JP)

(73) Assignee: Riken, Saitama (JP)

( * ) Notice: Subject to any disclaimer, the term of this patent is extended or adjusted under 35 U.S.C. 154(b) by 365 days.

(21) Appl. No.: 10/498,341

(22) PCT Filed: Dec. 16, 2002

(86) PCT No.: PCT/JP02/13124

§ 371 (c)(1),
(2), (4) Date: Mar. 18, 2005

(87) PCT Pub. No.: WO03/051804

PCT Pub. Date: Jun. 26, 2003

(65) Prior Publication Data

US 2005/0176824 A1 Aug. 11, 2005

(30) Foreign Application Priority Data

Dec. 17, 2001 (JP) .............................. 2001-382539

(51) Int. Cl.
*A61K 31/225* (2006.01)
*C12P 7/02* (2006.01)
*C12P 7/18* (2006.01)
*C07C 69/00* (2006.01)
*C07C 39/18* (2006.01)

(52) U.S. Cl. ..................... 514/548; 435/155; 435/158; 560/144; 568/780

(58) Field of Classification Search ................. 514/548, 514/733; 435/135, 155, 158; 560/144; 568/780
See application file for complete search history.

(56) References Cited

FOREIGN PATENT DOCUMENTS

WO 94/22863 10/1994
WO 01/68570 9/2001

OTHER PUBLICATIONS

Gerht et al, Cycloepoxydon, 1-Hydroxy-2-hydroxymethyl-3-pent-1-enylbenzene and 1-Hydroxy-2-hydroxymethyl-3-pent-1,3-dienylbenzene, New Inhibitors of Enkaryotic signal transduction, the J. of Antibiotics, 1998, vol. 51. No. 5, p. 455-463.*
Database Beilstein 'Online!, XP002353575, retrieved from Crossfire Beilstein Database accession no. 3280058.
Nishiwaka, Bulletin of the Agricultural Chemical Society of Japan, vol. 9, 1933, pp. 148-151.
Y. Hamada et al., Tetrahedron, vol. 47, No. 40 pp. 8635-8652, 1991.
R.S. Mali et al., J. Chem. Soc. Commun., No. 12, pp. 883-884, 1992.
J.M. Brown et al., Cancer Research, vol. 58, Apr. 1, 1998, pp. 1408-1415.
G.L. Semenza, Trends in Molecular Medicine, vol. 7, No. 8, Aug. 2001, pp. 345-350.
P.A. Baeuerle et al., Cell, vol. 87, Oct. 4, 1996, pp. 13-20.
P.A. Baeuerle, Cell, vol. 95, Dec. 11, 1998, pp. 729-731.
H. Sasaki et al., Toxicology, vol. 155, 2000, pp. 27-35.

* cited by examiner

*Primary Examiner*—Taylor Victor Oh
(74) *Attorney, Agent, or Firm*—Greenblum & Bernstein, P.L.C.

(57) ABSTRACT

A compound represented by the following formula (I) or a salt thereof which has excellent antitumor activity and angiogenesis inhibitory action in a low oxygen condition, and a medicament such as an antitumor agent and an anti-inflammatory agent which comprises the compound or a physiologically acceptable salt thereof as an active ingredient.

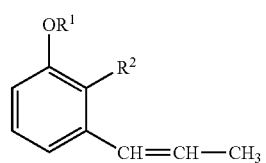

(I)

6 Claims, No Drawings

SUBSTANCE HAVING ANTITUMOR/ANTI-INFLAMMATORY ACTIVITY

TECHNICAL FIELD

The present invention relates to novel compounds which are useful as active ingredients of medicaments such as antitumor agents and anti-inflammatory agents.

BACKGROUND ART

Most anticancer agents clinically used at present have problems such as appearance of cancer cells with acquired resistance, i.e., anticancer agents that were effective formerly loose the effectiveness, and insufficient effectiveness against solid cancers. The tendency of the insufficient effectiveness of anticancer agents against solid cancers is considered to be caused by the activation or the like of transcription factors such as hypoxia inducible factor-1 (HIF-1) and nuclear factor κB (NF-κB) and resulting induction of excess expression of survival signals when a solid cancer grows larger than a certain size so as to cause internal hypoxic condition [Cancer, Res. 58, 1408 (1998)], and are activated to cause [Trends Mol. Med., 7, 345 (2001), Cell, 87, 13 (1996), Cell, 95, 729 (1998), Toxicology, 155, 27 (2000)]. However, details of the mechanism has not been clarified.

Under hypoxia (low oxygen pressure), a variety of genes, for example, erythropoietin which promotes generation of erythrocytes to increase oxygen supply to the whole body, VEGF and its receptor which stimulate angiogenesis to increase local oxygen supply, and genes of various enzymes in the glycolytic system which synthesize ATP in a condition without oxygen and provide resistance to cells, are activated to maintain homeostasis of oxygen. Hypoxia inducible factor-1 (HIF-1) is a chief transcription factor which performs transcription activation of these genes. Tumor tissues are in a low oxygen condition due to insufficient blood flow, and this low oxygen condition is known to accelerate angiogenesis. Accordingly, it is suggested that HIF-1 is deeply involved in angiogenesis.

Tumor necrosis factor α (TNF-α) is a major cytokine which exists in inflammatory sites and induces cell death through apoptosis. TNF-α stimulates generation of nuclear factor κB (NF-κB), and as a result, some types of cells have more potent resistance to the apoptosis signals. For example, in prostatic cancer and vesical cancer, cancer cells are hardly killed due to activation of NF-κB.

Therefore, if a substance is available that can inactivate HIF-1 or NF-κB which is excessively activated under a low oxygen condition or in an inflammatory site, the substance can be considered to be effective for preventive and/or therapeutic treatment of a solid cancer, chronic inflammation, and a variety of diseases caused by abnormal angiogenesis.

DISCLOSURE OF THE INVENTION

Accordingly, an object of the present invention is to provide novel compounds which exhibit antitumor activity even under a low oxygen condition.

Another object of the present invention is to provide a method for preparing novel compounds having the aforementioned feature, and medicaments which comprise said compound as an active ingredient.

The inventors of the present invention conducted various studies to achieve the foregoing objects. As a result, they found that a novel compound isolated from a fermentation mixture of strain BAUA3564 belonging to Eumycetes, and their analogues which were prepared from said compound by chemical synthesis (synthetic method) had antitumor activity even under a low oxygen condition. Thus, the inventors succeeded in providing medicaments which comprise said compound or an analogue thereof as an active ingredient to achieve the present invention.

The present invention thus provides a compound represented by the following formula (I) or a salt thereof:

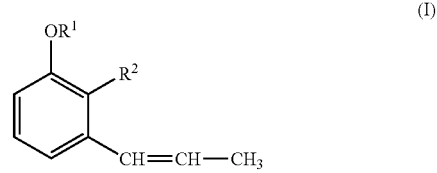

(I)

wherein $R^1$ represents hydrogen atom, an alkyl group, an alkenyl group, or —CO—$R^3$ (wherein $R^3$ represents an alkyl group, an aryl group, or an alkylamino group); $R^2$ represents formyl group, carboxyl group, —$CH_2$—$OCOR^4$ (wherein $R^4$ represents an alkyl group, an aryl group, or an alkylamino group), —$CH_2$—O—$R_5$ (wherein $R^5$ represents hydrogen atom, an alkyl group, or an alkenyl group), —$CH_2$=N—O—$R^6$ (wherein $R^6$ represents hydrogen atom or an alkyl group), or $CH_2$=CH—$R^7$ (wherein $R^7$ represents an alkyl group, an alkyloxycarbonyl group, formyl group, or an alkyloxycarbonylalkenyl group).

According to preferred embodiments of the invention, provided are a compound represented by the following formula (II):

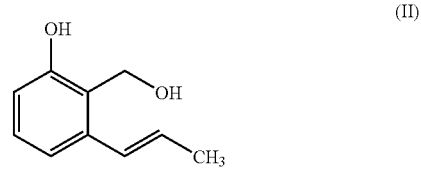

(II)

and a compound represented by the following formula (III):

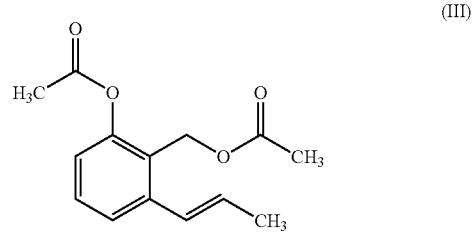

(III)

From another aspect of the present invention, provided are methods for preparing the compounds represented by the foregoing formulas (I) to (III) or salts thereof which comprise the step of culturing a filamentous fungi, which is a microorganism producing the compounds represented by the foregoing formulas (I) to (III), and separating and collecting the compounds from the resulting culture.

From a further aspect of the present invention, provided is a medicament which comprises the compound represented by the foregoing formulas (I) to (III) or a physiologically acceptable salt thereof as an active ingredient.

The medicament can be used as an antitumor agent, an anti-inflammatory agent, an immunosuppressant agent and the like, as well as a medicament for preventive and/or therapeutic treatment of a variety of diseases which are caused by a low oxygen condition, for example, a variety of diseases which are caused by abnormal angiogenesis accelerated by a low oxygen condition, and as an angiogenesis inhibitor in a tumor.

From another aspect of the present invention, provided are a use of the compound represented by the forgoing formulas (I) to (III) or a physiologically acceptable salt thereof for the manufacture of the forgoing medicament; and a method for preventive and/or therapeutic treatment and inhibition of a malignant tumor and an inflammation which comprises the step of administering an effective amount of the compound represented by the forgoing formulas (I) to (III) or a physiologically acceptable salt thereof to a mammal including a human.

BEST MODE FOR CARRYING OUT THE INVENTION

In the specification, "the alkyl group" may be a straight or branched chain alkyl group, a cyclic alkyl group, or a combination thereof. As the alkyl group, for example, an alkyl group having 1 to 6 carbon atoms, preferably a straight or branched chain alkyl group having 1 to 6 carbon atoms, can be used. More specifically, methyl group, ethyl group, n-propyl group, isopropyl group, n-butyl group, isobutyl group, sec-butyl group, tert-butyl group, n-pentyl group, n-hexyl group and the like can be used. An alkyl moiety of the other substituents having the alkyl moiety (e.g., an alkyloxycarbonyl group, an alkylamino group and the like) has the same meaning.

The aryl group may be a monocyclic aryl group or a condensed-ring aryl group. Examples include phenyl group, naphthyl group and the like. The number of the double bond contained in the alkenyl group is not particularly limited, and the number is, for example, about 1 to 3, and preferably 1 or 2. An alkenyl moiety of the alkyloxycarbonylalkenyl group containing the alkenyl group has the same meaning. The alkylamino group may be a monoalkylamino group or a dialkylamino group, and the two alkyl groups existing in the dialkylamino group may be the same or different.

The alkyl group, the aryl group, the alkylamino group, the group represented by —$CH_2$—O—$R^5$, the group represented by —$CH_2$=N—O—$R^6$, or the group represented by $CH_2$=CH—$R^7$ may have one or more substituents. The number, position and sort of the substituent are not particularly limited. Examples of the substituent include a halogen atom, an alkyl group, an alkoxy group, an aryl group, amino group, hydroxyl group, oxo group and the like.

Depending on the types of $R^1$ and $R^2$ which are substituents in the formula (I), stereoisomers such as optical isomers and diastereomers based on asymmetric carbon atoms and the like exist. The pure stereoisomers as well as mixtures of any stereoisomers or racemates fall within the scope of the present invention. Moreover, geometrical isomers based on the geometrical isomerization of the olefinic double bond exist, and the geometrical isomers in a pure form as well as mixtures of any geometric isomers fall within the scope of the present invention.

In addition to the compounds of the present invention in a free form, salts of the forgoing compounds, preferably physiologically acceptable salts fall within the scope of the present invention. The form of the salt is not particularly limited. For example, the compound of the formula (I) may sometimes form a sodium salt or the like with the phenolic hydroxyl group. Furthermore, hydrates or solvates of the forgoing compounds or salts thereof fall within the scope of the present invention.

Among the compounds represented by the formula (I), preferred compounds are those represented by the forgoing formulas (II) and (III). In the specification, the compound represented by the formula (II) may sometimes be referred to as RKB-3564S, and that represented by the formula (III) as RKB-3564SAC.

The compound represented by the formulas (I) to (III) according to the present invention can be separated and collected from a culture of a microorganism, or prepared by a method of chemical modification of the compound of the present invention as a starting material which is separated and collected from a culture of a microorganism. An example of the microorganism that can produce the compound of the present invention includes strain BAUA3564 which belongs to the class of filamentous fungi. The microorganism is cultured in a medium composition under a culture condition which is ordinarily used, and then the compound of the present invention contained in the culture can be separated and collected. The strain has been deposited as international deposition under Budapest Treaty in Patent and Bio-Resource Center of National Institute of Advanced Industrial Science and Technology (Chuo-6, 1-1-1, Higashi, Tsukuba, Ibaraki, Japan) with the accession number of PERM BP-8001 on Apr. 5, 2002 (said deposition has been transferred from the deposition under accession number of FERM P-18284 deposited in the aforementioned authority on Apr. 2, 2001).

As a medium for producing the compound of the present invention, any of synthetic mediums or natural mediums can be suitably used so long as they appropriately contain carbon sources, nitrogen sources, and inorganic salts. If necessary, mediums may be suitably supplemented with vitamins and other nutrient substances.

As the carbon source, one or more kinds of sources may suitably be chosen and used in consideration of auxotrophy of a microorganism from general carbon sources, for example, sugars such as glucose, maltose, fructose, sucrose, and starch, alcohols such as glycerol, and mannitol, amino acids such as glycine, alanine, and asparagine, and oils and fats such as soy bean oil and olive oil. Examples of the nitrogen source include organic nitrogen-containing compounds such as soy bean powder, corn steep liquor, beef extract, peptone, yeast extract, amino acid mixtures, and fish powder, and inorganic nitrogen compounds such as ammonium salts and nitrates, and one or more kinds of the sources may suitably be chosen and used in consideration of auxotrophy of a microorganism. As the inorganic salt, for example, calcium carbonate, sodium chloride, potassium chloride, magnesium sulfate, cupper sulfate, manganese chloride, zinc sulfate, cobalt chloride, and various phosphates may be added, if necessary. A defoaming agent such as vegetable fats and polypropylene alcohols can also be added, if necessary.

A cultivation temperature may appropriately be chosen and changed within a range that allows growth of a microorganism and effective production of the compound of the present invention. Preferred cultivation temperature is from 10° C. to 32° C., and more preferably from 20° C. to 25° C. pH at the beginning of the cultivation is preferably from about 6 to 8, and cultivation period of time is generally about one day to a few weeks. In general, the cultivation may be terminated when a produced amount of the compound of the present invention reaches to an amount suitable for collection, preferably reaches to the maximum amount. As a cultivation method, any method can be suitably employed so far that the method is an ordinarily used, such as solid layer cultivation and normal stirring cultivation.

In order to separate and collect the compound of the present invention from the culture liquid, any means ordinarily used for generally collecting microbial metabolites can be appropriately applied. Examples include chromatography with adsorbent such as various ion exchange resins, nonionic adsorbing resins, gel filtration chromatography, activated charcoal, alumina and silica gel, or a separation method by using high performance liquid chromatography, or crystallization, concentration under reduced pressure, or lyophilization, which means can be used alone or in appropriate combination thereof, or repeatedly.

The compound wherein $R^1$ is an alkyl group, or an alkenyl group, —CO—$R^3$ (wherein $R^3$ is as mentioned above), $R^2$ is formyl group, carboxyl group, —$CH_2$—$OCOR^4$ (wherein $R^4$ is as mentioned above), —$CH_2$—O—$R^5$ (wherein $R^5$ is as mentioned above), —$CH_2$=N—O—$R^6$ (wherein $R^6$ is as mentioned above), or $CH_2$=CH—$R^7$ (wherein $R^7$ is as mentioned above) can be prepared by using the compound of the present invention as a starting material which is separated and collected from the culture (e.g., RKB-3564S and the like), and performing functional group conversion which is well-known to a person with ordinary skill in the art.

For example, the compound wherein $R^1$ is —CO—$R^3$ can be prepared by carrying out an ordinary esterification reaction using an acylating agent (e.g., acetyl chloride and the like) from the compound wherein $R^1$ is hydrogen atom. The compound wherein $R^1$ is an alkyl group or an alkenyl group can be prepared by carrying out an ordinary alkylation or alkenylation reaction using an alkyl halide (e.g., methyl iodide and the like) or an aryl halide (e.g., propargyl bromide and the like) from the compound wherein $R^1$ is hydrogen atom. The compound wherein $R^2$ is formyl group or carboxyl group can be prepared by carrying out an ordinary oxidation reaction. The compound wherein $R^2$ is —$CH_2$—$OCOR^4$ (wherein $R^4$ is as mentioned above) can be prepared by carrying out an ordinary esterification reaction of the compound wherein $R^2$ is hydroxymethyl. The compound wherein $R^2$ is $CH_2$—O—$R^5$ (wherein $R^5$ is as mentioned above) can be prepared by carrying out an ordinary alkylation reaction of the compound wherein $R^2$ is hydroxymethyl. The compound wherein $R^2$ is —$CH_2$=N—O—$R^6$ (wherein $R^6$ is as mentioned above) can be prepared by converting $R^2$ of the compound wherein $R^2$ is hydroxymethyl to formyl group, and then reacting with hydroxylamine or the like. The compound wherein $R^2$ is —$CH_2$=CH—$R^7$ (wherein $R^7$ is as mentioned above) can be prepared by converting $R^2$ of the compound wherein $R^2$ is hydroxymethyl to formyl group, and then subjecting the resulting compound to the ordinary Wittig reaction. In the aforementioned reactions, reaction conditions, reagents and the like can suitably be chosen by one of ordinary skill in the art.

The compound of the present invention exhibits excellent antitumor activity in a low oxygen condition as described in the examples mentioned later. Accordingly, the compound of the present invention is useful as an antitumor agent, as well as an anti-inflammatory agent, an immunosuppressant agent, and a medicament for preventive and/or therapeutic treatment of a variety of diseases caused by a low oxygen condition. Examples of the disease caused by a low oxygen condition include so-called "angiogenetic diseases" which are deeply involved in abnormal angiogenesis accelerated by a low oxygen condition, specifically, psoriasis, chronic articular rheumatism, rheumatoid arthritis, diabetes, myocardial infarction, ulcerative colitis, eye diseases such as angiogenetic glaucoma, arteriosclerosis, diabetic vascular complications, diabetic retinopathy and the like. In addition, the medicament of the present invention can also be used as an inhibitor of angiogenesis in a tumor.

A route of administration, a dosage form, and a dose of the medicament of the present invention can be appropriately chosen depending on a purpose of administration. The route of administration of the medicament of the present invention may be oral administration or parenteral administration. The form of the medicament of the present invention is not particularly limited, and examples include oral preparations such as fine powders, powders, granules, tablets, capsules, pills, and solutions, and parenteral preparations such as injections, suppositories, percutaneous absorption agents, and inhalants. These preparations can be manufactured as pharmaceutical compositions according to known methods, if necessary, by mixing pharmaceutical additives such as excipients, binders, moisturizers, disintegrating agents, and lubricants which are suitable for the dosage form. For injections, the medicament is subjected to a sterilizing treatment with an appropriate carrier to give the preparation. A dose is usually from 0.1 to 100 mg/kg/day, preferably from 1 to 20 mg/kg/day for oral administration for an adult, and from 0.01 to 10 mg/kg/day, preferably from 0.1 to 2 mg/kg/day for parenteral administration, which may be increased or decreased depending on the state of a disease, the administration route, and the age and body weight of a patient, and which is finally decided by a doctor. The dose may be administered once a day or several times a day as divided portions.

When the compound of the present invention is used as a reagent, the compound can be used by dissolving said compound in an organic solvent or a water-containing organic solvent. For example, cell growth can be inhibited by direct application to various culture cancer cell systems under a low oxygen condition. Examples of usable organic solvent include methanol, dimethyl sulfoxide and the like. Examples of the reagent form include solid preparations such as powders, or liquid preparations dissolved in an organic solvent or a water-containing organic solvent. When the aforementioned compound is used as a reagent for exerting cancer cell growth inhibitory action under a low oxygen condition, an effective amount is usually from 0.1 to 100 µg/ml. An appropriate amount may differ depending on a type of a culture cell system and a purpose of using the reagent, which can suitably be chosen. The amount out of the aforementioned range can be applied, if necessary.

EXAMPLES

The present invention will be explained more specifically by referring to the following examples and experimental examples. However, the present invention is not limited thereto.

Example 1

Strain BAUA3564 belonging to Oidiomycetes was inoculated into a medium comprising glucose 1.0%, soluble starch 2.0%, soy bean powder 1.5%, malt extract 0.5%, vegetable extract 10%, potassium diphosphate 0.05%, potato dextrose 2.6%, and magnesium sulfate 0.05%, and then cultivation was carried out with shaking at 28° C. for 72 hours. The culture liquid (210 ml) was inoculated to a medium of the same composition (15 liters), and cultivation was carried out with shaking at 28° C. for 96 hours.

The aforementioned culture liquid was separated into bacterial mass and a supernatant by using a centrifugal separator, and the supernatant was adjusted to pH 7.0 and extracted with 15 liters of ethyl acetate. After extraction, all ethyl acetate layers were combined and concentrated under reduced pressure to give brown syrup (5.3 g). The syrup was dissolved in chloroform (10 ml) and applied to a silica gel column charged with chloroform (4 cm diameter, 60 cm length). Initially, elution was performed with chloroform (600 ml), then with each 600 ml of a chloroform/methanol solution having a successively changed mixing ratio (100:1, 50:1, 20:1, 10:1, 5:1, 1:1).

The compound of the present invention, RKB-3564S, was eluted in a fraction with the chloroform/methanol solution (50:1). The fraction was concentrated under reduced pressure to give brown syrup (1.1 g). Then, the brown syrup (1.1 g) was dissolved in methanol (11 ml) and made into aliquots, and purified by high performance liquid chromatography (acetonitrile: water=2:8→acetonitrile:water=6:4; linear gradient, flow rate 9.0 ml/min) using a reverse phase ODS column (2 cm diameter, 25 cm length, PEGASIL ODS, Senshu Kagaku Co.) to obtain a fraction containing an active substance. Thin layer silica gel column chromatography (chloroform:methanol=20:1) was further carried out to give RKB-3564S (45 mg) as colorless powdery crystals.

The physico-chemical properties of RKB-8564S are shown below.
Appearance: colorless powdery crystals
Melting point: 71.5-72° C. (dec.)
Molecular formula: $C_{10}H_{12}O_2$
High-resolution mass spectrum (HR-RABMS): $(M+H)^{+Found}_{(m/z)}$: 165.0868 Calcd. (m/z): 166.0916 UV λ max nm (methanol) (e): 218 (45570), 250 (18030), 295 (4475) IR ν max (neat) $cm^{-1}$: 3220, 2910, 1580, 1465, 1255, 970 $R_f$ value (Silica gel 60 $F_{254}$, Merck): 0.34 (solvent; $CHCl_3$: methanol=20:1) Color reaction (positive): 10% sulfuric acid Solubility: easily soluble in methanol or dimethyl sulfoxide. Insoluble in n-hexane.

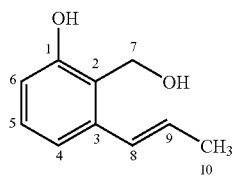

(II)

NMR data of RKB-3564S are shown in Table 1 (solvent: deuterated acetone, δ ppm, internal standard: TMS, $^{13}C$: 125 MHz, $^1H$: 500 MHz).

TABLE 1

| Position | $^{13}C$ (multiplicity) | $^1H$ | (J/Hz) |
|---|---|---|---|
| 1 | 157.32 s | | |
| 2 | 124.14 s | | |
| 3 | 139.03 s | | |
| 4 | 118.25 d | 6.90 d | 7.7 |
| 5 | 128.94 d | 7.08 dd | 7.7, 7.9 |
| 6 | 115.11 d | 6.69 d | 7.9 |
| 7 | 58.32 t | 4.84 br s | |
| 8 | 129.44 d | 6.72 dd | 1.8, 15.6 |
| 9 | 128.37 d | 6.07 dq | 6.7, 15.6 |
| 10 | 18.77 q | 1.84 dd | 1.8, 6.7 |

Example 2

A dichloromethane solution (1 ml) of RKB-3564S (1.8 mg, 0.011 mmol) was added with pyridine (4 μl) and acetic anhydride (10 μl), and the mixture was stirred at room temperature for 1 hour. Then, chloroform was added in the reaction mixture for dilution, and the chloroform layer was washed successively with 1N hydrochloric acid, distilled water, and saturated saline. The mixture was dried with anhydrous sodium sulfate, and then concentrated to dryness under reduced pressure, and the resulting oil was purified by thin layer chromatography to give RKB-3564SAC (2.8 mg) as colorless oil.

The physico-chemical properties of RKB-3564C are shown below.
FAB-MS(positive): m/z 249 $(M+H)^+$
$^1HNMR$: δ (acetone-$d_6$, ppm)
IR ν max (neat) $cm^{-1}$: 1.88 (1H, dd, 1.5, 6.7), 1.95 (3H, s), 2.26 (8H, s), 5.12 (2H, br S), 6.22 (1H, dq, 6.7, 15.6), 6.76 (1H, dd, 1.5, 15.6), 7.00 (1H, d, 7.7), 7.33 (1H, dd, 7.7, 7.7), 7.39 (1H, d, 7.7)
IR ν max (neat) $cm^{-1}$: 2910, 17835, 1545, 1360, 1185, 1020
$R_f$ value (Silica gel 60 $F_{254}$, Merck): 0.69 (solvent; $CHCl_3$: methanol=50:1)

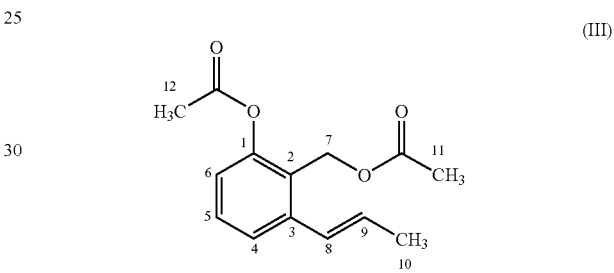

(III)

Test Example 1

Inhibitory Effect on Proliferation of Tumor Cells by RKB-3564S and RKB-3564SAC

MCF-7 cells derived from human mammary cancer were cultured in a RPMI medium (containing 5% bovine fetal serum). The cells were added with RKB-3564S and RKB-3564SAC in a series of dilution, cultured under the condition of 1% oxygen concentration or 20% oxygen concentration for 48 hours, then added with MTT reagent [3-(4,5-dimethyl-thiazol-2-yl)-2,5-diphenyltetrazolium bromide], and further cultured for 2 to 4 hours, and then the absorption at 570 nm was measured to calculate the survival rate. As a result, RKB-3564S and RKB-3564SAC in the concentration of 10 to 100 μg/ml significantly inhibited cell proliferation under the condition of 1% oxygen concentration compared to that under the condition of 20% oxygen concentration.

The result indicates that RKB-8564S and RKB-8564SAC according to the present invention exhibit remarkable cytocidal effects, and are effective as antitumor agents.

Test Example 2

Inhibitory Effect on NF-κB Activation by RKB-3564S and RKB-8564SAC

COS-7 cells maintained in a DMEM medium (containing 5% bovine fetal serum) were transfected with a plasmid (pGL3-NF1) containing 5xNF-κB binding sequence (5'-AGTTGAGGGGACTTTCCCAGGC-3') (SEQ ID NO: 1)

located upstream of the luciferase gene. The cells were added with TPA (50 ng/ml) and RKB-3564S and RKB-3564SAC in a series of dilution, and cultured for 24 hours, and then the activity of produced luciferase was measured to calculate the inhibitory effect on NF-κB activation by TPA. As a result, RKB-3564S and RKB-3564SAC in the concentration of 10 to 100 µg/ml inhibited transcription activation by NF-κB.

The result indicates that RKB-3564S and RKB-3564SAC according to the present invention are effective as anti-inflammatory agents, antitumor agents, immunosuppressants and the like.

Preparation Example 1

Injection and Drip Infusion

RKB-8564S or RKB-3564SA was aseptically divided and sealed in vials so as to contain 10 mg of the compound with powder glucose (5 g), and the vials were charged with an inert gas such as nitrogen and helium and stored in a cool and dark place. The preparation is dissolved in ethanol and added with 0.85% physiological saline (100 ml) before use to prepare an intravenous injection and administered by intravenous injection or drip infusion in the amount of from 10 to 100 ml per day depending on symptoms.

Preparation Example 2

Granules

RKB-8564S or RKB-3664SAC (1 g), lactose (98 g), and hydroxypropyl cellulose (1 g) were separately taken, well mixed, and then formed into particles according to a conventional method, and the particles were well dried to prepare granules suitable for a package in a bottle or a heat seal container. The granules can be orally administered in a dose of from 100 mg to 10 g per day depending on symptoms.

INDUSTRIAL APPLICABILITY

The compound of the present invention has excellent antitumor activity in a low oxygen condition. Accordingly, the compound of the present invention is useful as an active ingredient of an antitumor agent, especially an antitumor agent for a solid cancer against which an antitumor agent is hardly effective due to an internal low oxygen condition, as well as an anti-inflammatory agent, an immunosuppressant agent, a medicament for preventive and/or therapeutic treatment of a variety of diseases which are caused by a low oxygen condition, or an angiogenesis inhibitor in a tumor.

What is claimed is:

1. A compound represented by the following formula (I) or a salt thereof:

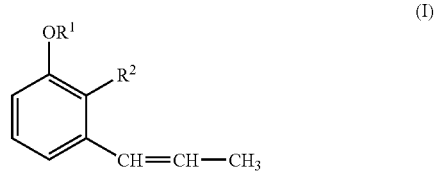

wherein $R^1$ represents an alkyl group, an alkenyl group, or —CO—$R^3$ (wherein $R^3$ represents an alkyl group, an aryl group, or an alkylamino group); $R^2$ represents formyl group, —$CH_2$—$OCOR^4$ (wherein $R^4$ represents an alkyl group, an aryl group, or an alkylamino group), —$CH_2$—O—$R_5$ (wherein $R^5$ represents an alkyl group, or an alkenyl group), —$CH_2$=N—O—$R^6$ (wherein $R^6$ represents hydrogen atom or an alkyl group), or $CH_2$=CH—$R^7$ (wherein $R^7$ represents an alkyl group, an alkyloxycarbonyl group, formyl group, or an alkyloxycarbonylalkenyl group).

2. A compound represented by the following formula (III):

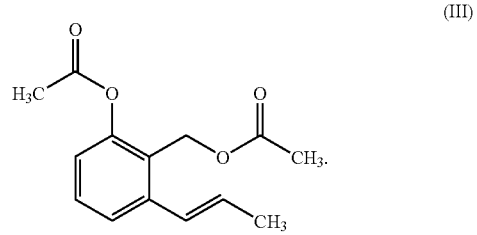

3. A method for preparing the compound according to claim 1, which comprises the step of culturing a filamentous fungi which produces the compound according to claim 1 and separating and collecting the compound from a resulting culture.

4. A method for preparing the compound represented by the following formula (II):

SEQUENCE LISTING

<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
agttgagggg actttcccag gc                                                22

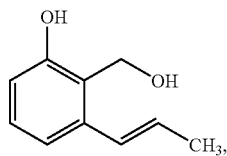

which comprises the step of culturing a filamentous fungus strain BAUA3564 which produces the compound and separating and collecting the compound from a resulting culture.

5. A method for preparing the compound according to claim 2, which comprises the step of culturing a filamentous fungi which produces the compound according to claim 2 and separating and collecting the compound from a resulting culture.

6. A medicament composition which comprises the compound according to claim 2 or a physiologically acceptable salt thereof as an active ingredient, further comprising at least one pharmaceutically acceptable additive.

* * * * *